(12) United States Patent
Livingston

(10) Patent No.: US 7,396,801 B1
(45) Date of Patent: Jul. 8, 2008

(54) MOSS CONTROL COMPOSITION

(75) Inventor: David W. Livingston, Julian, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/532,687

(22) Filed: Mar. 22, 2000

(51) Int. Cl.
*A01N 59/06* (2006.01)
*A01N 59/16* (2006.01)
*C05C 9/00* (2006.01)

(52) U.S. Cl. .......................... 504/121; 504/152; 71/28

(58) Field of Classification Search ................ 504/120, 504/121, 152; 71/28, 54, 63, 64
See application file for complete search history.

(56) References Cited

U.S. PATENT DOCUMENTS

| 3,964,893 | A |   | 6/1976 | Everingham et al. |        |
|-----------|---|---|--------|-------------------|--------|
| 4,214,888 | A | * | 7/1980 | Young             | 71/28  |
| 4,276,732 | A |   | 7/1981 | Nielsen           |        |
| 4,297,130 | A | * | 10/1981| Moore, Jr.        | 504/327|
| 4,507,142 | A | * | 3/1985 | Pace et al.       | 504/147|
| 4,936,898 | A |   | 6/1990 | Nielsen           |        |
| 5,009,700 | A |   | 4/1991 | Rothgery          |        |
| 5,021,247 | A | * | 6/1991 | Moore             | 426/69 |
| 5,108,481 | A |   | 4/1992 | Shutt             |        |
| 5,139,561 | A |   | 8/1992 | Talbot et al.     |        |
| 5,589,229 | A |   | 12/1996| Howard            |        |
| 6,458,747 | B1| * | 10/2002| Kulik             | 504/140|

OTHER PUBLICATIONS

Happ, Keith A., "Moss Eradication In Putting Green Turf", *USGA Green Section Record*, Sep./Oct. 1998.

* cited by examiner

*Primary Examiner*—Alton Pryor
(74) *Attorney, Agent, or Firm*—Woodard, Emhardt, Moriarty, McNett & Henry LLP

(57) ABSTRACT

The present invention is an aqueous composition for controlling or eradicating moss from undesirable locations such as lawns and golf course putting greens. The composition contains a fertilizer, a metal containing salt, a surfactant or wetting agent, and optionally, an acidic pH control agent. The composition can be provided in a form to be mixed and/or diluted by the end-user or in an aqueous form ready to be sprayed onto the infected area. Since the product can be broadly applied and encourages grass growth and development, it provides significant advantages over conventional moss control products intended for spot treating only.

4 Claims, No Drawings

MOSS CONTROL COMPOSITION

FIELD OF THE INVENTION

The present invention relates to the field of chemical compositions to control or eradicate moss growing in lawns, golf course putting greens and other locations where moss is undesirable.

BACKGROUND OF THE INVENTION

Moss grows in many undesirable areas including lawns, golf course putting greens, other landscaped areas, and on structures such as walls, building foundations, monuments, and the like. Moss growing on structures is relatively easy to control using harsh chemicals, but moss is particularly hard to control or eradicate is areas that also contain desirable plants such as grasses. As a result, moss is especially a growing concern among homeowners, professional landscapers, and golf course superintendents.

Moss growing amongst grass and other desirable plants is a major concern for a number of reasons. Foremost among these is that moss detracts from the attractiveness of well-maintained lawns and other landscaped areas. Moss also tends to retain moisture and can decrease the usefulness of a lawn area. Additionally, under certain conditions, moss tends to spread easily and will crowd out other desirable plants, especially grasses.

Moss is a photosynthesizing terrestrial plant. Mosses are non-vascular plants so they need to be in contact with water to avoid drying out. Many mosses absorb water over their entire surface area and they are generally adapted to shady, moist locations. However, some mosses can survive long periods of desiccation (sometimes several years) and can withstand high temperatures in a dormant state. Laboratory studies have shown that mosses can tolerate dehydration levels equal to 80% of original biomass. When mosses are rehydrated, an immediate respiratory burst occurs, but recovery is slow.

While we have used the term "moss" in a generic sense, it has been reported that thousands of species of mosses exist. Moss can develop and thrive in many different environments, but areas that have poor soil conditions, lots of shade, and are damp tend to be the best for moss growth. Many of the moss varieties are known to infest home lawns, but the types that are known to infest golf course putting greens are more limited in number. In particular, it has been found that there are four moss varieties that often inhabit golf course putting green turf. They are *Byrum argentums, Byrum lisae, Amblystegium trichopodium*, and *Brachythecium spp* (Happ, K., USGA Green Section Record, September 1998). *Byrum argentum* (or silvery thread moss) is found in open sites and is one of the most common contaminants of putting green turf. It can generally be easily distinguished from other mosses because of its silvery appearance.

The presence of moss on putting greens is a special problem because of the unique conditions found in these areas. Golf course superintendents are faced with many turf management decisions, most of which are centered on providing the best possible playing conditions. This usually involves mowing the putting green grass (typically a short growing bentgrass variety) as short as reasonably possible. The shorter the putting green grass is, the faster the ball tends to travel. Faster putting surfaces tend to be the most desirable among golfers. Consequently, the health of putting green turf is compromised in order to deliver the desired playing effect.

Seeking maximum surface performance by cutting the greens short can lead to reduced bentgrass vigor. The shorter the greens are cut and the lower the bentgrass vigor, the better the conditions are for moss development and growth. A small moss colony can proliferated and turn into a bigger problem that is more difficult to overcome. One reason that moss on bentgrass putting greens proliferates is because of re-infestation by golfers and greens maintenance equipment that inadvertently carry the spores to new locations. If conditions remain favorable for moss growth, the moss can spread across a putting surface and severely lower playing conditions. The challenge for golf course superintendents is to eliminate moss infestation without compromising the health of putting green surfaces.

Despite these problems, the solutions for controlling or eradicating moss from lawns, golf course putting greens, and similar areas has remained rather limited and unsatisfactory. A few products exist that have been used to control moss to some extent, but to our knowledge, there are no commercially available products that effectively kill moss over a broad area without damaging the turf. These products are typically powdered forms of certain metallic salts such as iron, zinc, and copper-sulfur compounds. They provide varying degrees of success, but also have significant drawbacks. Such powdered compositions are generally used only for spot treatment as they are difficult to apply over a broad area. While they can sometimes be put into solution, the concentration required to kill the moss colonies tends to be harmful to the grass. Additionally, we know of a liquid product called DeMoss™ sold by Mycogen Corporation that is advertised as a moss control product. This product is a potassium salt of fatty acid.

In addition to the known commercial products several inventors in the patent literature have created methods to control moss in lawns and on structures. Some examples of these methods are briefly discussed below.

U.S. Pat. No. 5,139,561 to R. Talbot and K. Cooper discloses a method for protecting growing plants, including grasses, from fungal or microbial pathogens using a composition containing tetrakis (hydroxymethyl) phosphonium salt. One particular application of the composition is for control of mosses in lawns.

U.S. Pat. No. 4,276,732 to J. Nielsen discloses a device for killing moss on rooftops. In one embodiment, the device comprises a trough made of a layer of lead and copper. As rainwater filters through holes in the trough, an electrolytic action occurs in which ions of the metals dissolve into the water. The resultant aqueous electrolyte kills moss growing on the roof.

U.S. Pat. No. 5,009,700 to Rothgery describes a process for ridding moss from unwanted locations such as lawns, walls, monuments, building foundations, tombstones, and the like. The process comprises contacting the moss growing in said unwanted locations with an effective amount of a pyrithione salt. The composition optionally includes a surfactant or wetting agent.

U.S. Pat. No. 5,108,481 to T. Shutt discloses a method of making a pelletized ferrous sulfate. It is further disclosed that the pelletized ferrous sulfate may be used as a moss-control agent.

U.S. Pat. No. 3,964,893 to J. Everingham and K. Hoenke teaches a lawn moss control composition comprising a granular ferric ammonium sulfate-ammonium sulfate double salt. The patent further discloses that the ferric double salt is as effective as ferrous ammonium sulfate for promoting the greening of turf grass.

U.S. Pat. No. 5,589,229 to R. Howard discloses a composition and method for preventing moss growth on roofs. The composition is an aqueous solution containing sodium oxide, silicon dioxide and a surfactant that is sprayed on the surface to be protected from moss growth.

U.S. Pat. No. 4,936,898 to J. Nielsen discloses a method for killing moss growing on a surface by using a moss-killing powder containing an atomized elemental metal which slowly dissolves with water to form a biocidal solution which kills the moss. The powder is essentially a mixture of elemental zinc and copper mixed with a powdered carrier such as silica clay.

In addition to these commercial and patented chemical methods, manual methods of moss removal from grass is commonly used. For example, a non-chemical method for the control of moss in lawns is to rake out the moss, fertilize the ground, and re-seed with grass. This raking method is time consuming and hard on the grass. This method and other manual methods of moss removal can not be accomplished without also damaging the lawn. Accordingly, it would be desirable to provide a simpler moss treatment method that selectively eradicates moss in a lawn, golf course putting green, or other area, without harming the co-located grasses.

None of the known commercial products or the products described in the patent literature and discussed above are fully satisfactory in meeting the current needs of homeowners, professional landscapers, and golf course superintendents. The present inventors have discovered a composition that more fully meets those needs by providing a convenient and effective moss control composition that does not damage grasses.

SUMMARY OF THE INVENTION

Accordingly, it is an object of this invention to provide an effective composition for controlling or eradicating moss in lawns, golf course putting greens, and other similar landscaped or turf containing areas.

It is an additional object of this invention to provide a method of controlling or eradicating moss that is more effective than spot treating by providing a liquid moss control composition that can be conveniently sprayed upon a broad area needing treatment.

It is still a further object of this invention to provide a moss controlling composition that will not harm the grass in the treatment area.

It is still a further object of this invention to provide a moss controlling composition that can be sprayed using conventional spraying equipment.

The present inventor accomplishes these and other objectives with a novel composition that is an aqueous solution that is sprayed on the area to be treated and efficiently kills moss while enhancing the health of the turf. The composition eradicates the moss while providing fertilizer to the grass so that it can reclaim areas taken over by the spreading moss. During treatment the turf may take on a dark green or blackish appearance due to the fertilizer and the iron sulfate in the product. The effect of the treatment is dramatic and the moss colonies begin to experience a desiccating effect and the turf gradually encroaches the moss colonies. The first signs of the decaying moss are exhibited by a blackish coloration.

The present invention is an aqueous solution comprising: (1) fertilizer, (2) a surfactant or wetting agent, and (3) a metal containing salt. Additionally, the composition can optionally contain an acidic pH-adjusting ingredient. Further, the product can be provided in concentrated form in one or more parts intended to be mixed and/or diluted with water by the end-user prior to use.

When the composition of the present invention is applied to lawns and golf course putting greens, it has been surprisingly found that the moss is effectively eliminated after only a few treatments without damage to the grasses growing in the treated areas.

The foregoing and other objects, features and advantages of the invention will become apparent from the following detailed description of several embodiments of the invention.

DETAILED DESCRIPTION OF THE INVENTION

The present composition is an aqueous product for spraying on lawns and putting greens comprising a fertilizer, a surfactant or wetting agent, and a metal containing salt. The composition can optionally contain an acidic pH adjusting ingredient.

The fertilizer used in the invention is not particularly limiting and any fertilizer that provides sufficient nutrients to enhance grass vigor during the moss eradication treatments will work. Preferred fertilizers contain a high concentration of nitrogen. Such fertilizers are commonly known to those skilled in the art of turf maintenance. Some non-limiting preferred liquid fertilizers include Coron™ by Helena Chemicals and an isobutylenediurea (IBDU) fertilizer by Parex/Lebanon Seaboard Company. The amount of fertilizer included in the aqueous composition is such that about 0.1 to 8 pounds of fertilizer (as nitrogen) is applied per 1000 square feet of treatment area. A preferred range is 0.1 to 5 pounds of nitrogen applied per 1000 square feet of treatment area. In an even more preferred embodiment the range is 0.5 to 3 pounds of nitrogen applied per 1000 square feet of treatment area. However, it is understood by the skilled individual that the optimum amount of each of the ingredients will be determined by the conditions of the treatment surface including the variety of the grass(es) growing in the treatment area.

In a preferred embodiment, the present inventor has found that a slow-release nitrogen containing fertilizer is especially effective in the invention. One particular example of such a fertilizer is isobutylenediurea (IBDU) supplied by Parex/Lebanon Seaboard Company.

The type of surfactant or wetting agent used in the present invention is limited only in the sense that it must provide the composition with the ability to sufficiently wet the surface of the moss in order to enhance the biocidal action of the solution. Anionic, cationic, and non-ionic surfactants will all work in the present invention. Such surfactants are commonly known to the skilled artisan and do not need to be repeated in detail here.

The amount of surfactant or wetting agent used in the present invention can also vary widely with the major requirement being only that the composition contains an amount sufficient to wet the moss surface enough to enhance the killing effect of the other ingredients. However, in general the amount of surfactant or wetting agent included in the composition is sufficient to provide from 0.1–50 fluid ounces of the liquid surfactant per 1000 square feet of surface treated. In a preferred embodiment the range is 0.1 to 35 fluid ounces, and more preferably 1 to 25 fluid ounces applied per 1000 square feet of treatment area. The optimum amount of surfactant to use will be determined by, among other things, the type of surfactant, the variety of grass and moss and other conditions of the treatment area.

In a preferred embodiment, a non-ionic wetting agent is used. We have found Aqueduct™ and Primer™ 604 liquid non-ionic wetting agents from Aquatrols, Cherry Hill, N.J. to be highly effective. The Aqueduct™ product comprises a 50% blend of non-ionic polyols, 5% 1,2 propanediol, and 45% water. The Primer® 604 product is 95% polymeric polyoxyalkylenes and 5% oxoalkenyl hydroxy polyoxyalkane diyl.

The metal salt used in the present invention can be any metal salt that exhibits a killing or desiccating effect on growing moss. Non-limiting examples of such salts include iron, copper, and zinc containing salts, which have all been shown to be harmful to mosses. The second component of the salt is typically a phosphate or a sulfate. In a preferred embodiment, the salt is a metal sulfate and in an especially preferred embodiment, the desired salt is ferrous sulfate.

The amount of metal salt in the present invention is an amount sufficient to inhibit the growth or spread of the moss in the turf but less than an amount that will kill or severely harm other desirable plants (e.g. grasses) growing in the treatment area. Preferably the amount is sufficient to kill most of the moss after only a few treatments without harming the turf. The amount used will likely vary considerably depending on the variety of grass(es) in the treatment area because some varieties are much more sensitive than others. In general the amount of the metal salt will be within the range of 0.1 to 80 ounces (by weight) applied per 1000 square feet of treatment area. A preferred range of metal salt is 0.1 to 60 ounces and in an even more preferred embodiment, the amount lies within the range of 1 to 50 ounces applied per 1000 square feet of treatment area. Additionally, the metal salt (e.g. ferrous sulfate) is typically supplied in a powder form and must be dissolved or suspended in water prior to use. In such instances, it is typically the case that finer powders show a greater tendency to dissolve or suspend in water.

Optionally, an acidic pH adjusting agent is included in composition of the present invention. The amount of this ingredient is not particularly limited. We have found it sufficient to add a dilute weak acid in an amount that moderately lowers the pH of the composition. Acids of the types known as mineral acids, organic acids, or Lewis acids can be used. Some non-limiting examples include: hydrochloric acid, phosphoric acid, citric acid, acetic acid, and tartaric acid. In one embodiment, we have used a 5% (by volume) solution of acetic acid (vinegar) because of its low cost and ready availability. The amount of this dilute acid included in the composition will be such that from 0.1 to 80 fluid ounces (of the 5% solution) will be applied per 1000 square feet of treatment area. Preferably enough acid is added to adjust the pH in the range of 2 to 6, more preferably in the range of 2.5 to 5 and most preferably in the range of about 3 to about 4.

Additionally, it should be noted that the composition can contain other common ingredients to enhance the appearance and/or performance of the product. Such ingredients are known to those skilled in the art of agricultural or turf management chemical compositions. Some examples include suspending agents and similar ingredients to enhance the shelf life of the product, non-nitrogen containing fertilizers, insecticides, colorants, fragrances, solvents, thinning agents, and thickening agents to give a few non-limiting examples.

Further, the composition of the present invention can be supplied to the consumer in a diluted ready-to-use form or can be supplied in a concentrated form needing dilution with water by the end-user. Additionally, the product can be supplied in two or more parts to the consumer to be mixed and/or diluted by the consumer prior to use. The latter form of the invention may be done to enhance the shelf of the product since some metal salts do not stay suspended very well in liquid compositions.

The invention will now be described in the following illustrative examples. The examples are given for illustrating preferred embodiments of the invention and are not meant to be limiting in any way of the scope of applicant's invention.

Experiment 1

This experiment was conducted on a sand-based putting green at the Joseph Valentine Turfgrass Research Center at The Pennsylvania State University, University Park, Pa. The green was a stand of Pennlinks™ creeping bentgrass (*Agrostis palustris*) and *Poa annua* mowed at $5/32^{nd}$ of an inch (bench setting) with a triplex mower. The green was fertilized, watered, and treated with pesticides to maintain acceptable turf quality prior to the study.

The test site selected had a good moss population ranging in size from $1/8^{th}$ inch diameter up to 3 inch diameter colonies. Cultural practices such as aerating, spiking, and verticutting were not performed during the study to prevent mechanical injury and stress to the moss. The experimental design was a randomized complete block design replicated three times. Each individual plot was 3 by 10 feet. An initial moss count was taken on June 24 to determine the amount of moss in each plot. Each of the formulations were liquid and sprayed using a $CO_2$ powered walk behind sprayer equipped with a three-foot boom, and TeeJet 8008 flat fan nozzles. The sprayer was calibrated to deliver 4 gal./1000 sq. ft. The sprayer was rinsed out between each treatment.

One of the nine formulations (seen Table 1) was applied to each of the twenty-seven plots. A total of five applications were made to each plot at about two week intervals. The applications began on June $23^{rd}$ and a final application was made on August $20^{th}$. The final moss count was taken on September $18^{th}$ (29 days after the final application).

TABLE 1

Moss Control Formulation in Experiment 1

| Formula | Components | Amount Applied (/1000 sq ft.) |
| --- | --- | --- |
| 1 | Acid | 38.2 oz. |
| 2 | Ferrous Sulfate | 33.3 oz. |
| 3 | Acid + Ferrous Sulfate | 38.2 oz.; 33.3 oz. |
| 4 | Acid + Fertilizer | 38.2 oz.; 2/3 lb. N |
| 5 | Acid + Fertilizer + Wetting Agent | 38.2 oz.; 2/3 lb. N; 14.5 oz. |
| 6 | Ferrous Sulfate + Fertilizer | 33.3 oz.; 2/3 lb. N |
| 7 | Ferrous Sulfate + Fertilizer + Wetting Agent | 33.3 oz.; 2/3 lb. N; 14.5 oz. |
| 8 | Acid + Ferrous Sulfate + Fertilizer + Wetting Agent | 38.2 oz.; 33.3 oz.; 2/3 lb. N; 14.5 oz. |
| 9 | Control (untreated) | N/A |

The acid used was a 5% by volume solution of acetic acid (vinegar). The ferrous sulfate was a fine grade ferrous sulfate powder supplied by Agway. The fertilizer used was a sprayable IBDU 30-0-0 formulation from Lebanon Seaboard and the wetting agent used was a non-ionic Aqueduct™ made by Aquatrols, Inc. The entire composition was diluted so that four gallons of composition would contain the amounts specified in Table 1. The composition was applied at a rate of four gallons per 1000 square feet of treatment area.

It was observed that Formulations 2, 3, 6, 7, and 8 darkened the turf color because of the ferrous sulfate component in those composition. This condition lasted for two to three days. Moss color in these plots turned black following application, but began to "green-up" at the surface prior to the next application. With each subsequent application, the moss turned black again and less moss recovered. Additionally, it was qualitatively noticed that formulations with the fertilizer component stimulated turf growth, which aided in the turf's ability to fill in the voids left by the eradicated moss.

Table 2 shows the results of the experiment by the average reduction in the number of moss colonies larger than about $1/8^{th}$ of an inch. The average was taken across three plots for each formulation. For formula 8 it was observed that moss infections of about $3/4^{th}$ of an inch and smaller were completely eliminated after three applications. More applications were required to eradicate moss colonies larger than $3/4^{th}$ inch. Also, it was noted that as the summer progressed, there was a natural decline in the moss population as can be seen from the 25% reduction observed for the untreated plots. The plots that were sprayed with treatments that included fertilizer in the formulation were more dense, aggressive, and healthy. The best formulation was the composition containing acid, ferrous sulfate, fertilizer and wetting agent. This formulation nearly completely eradicated the moss from the plots.

TABLE 2

Reduction in Moss Populations

| Formula | Components | Average Moss Reduction |
|---|---|---|
| 1 | Acid | 74.3% |
| 2 | Ferrous Sulfate | 86.1% |
| 3 | Acid + Ferrous Sulfate | 77.3% |
| 4 | Acid + Fertilizer | 34.2% |
| 5 | Acid + Fertilizer + Wetting Agent | 49.1% |
| 6 | Ferrous Sulfate + Fertilizer | 91.9% |
| 7 | Ferrous Sulfate + Fertilizer + Wetting Agent | 91.2% |
| 8 | Acid + Ferrous Sulfate + Fertilizer + Wetting Agent | 98.5% |
| 9 | Control (untreated) | 25.3% |

Experiment 2

A second experiment was conducted to qualitatively test the safety and effectiveness of the present invention on a large variety of bentgrasses. This test was performed on the creeping bentgrass putting green variety trial at The Pennsylvania State University's Joseph Valentine Turfgrass Research Center. The test area is over 12,000 square feet containing 125 different creeping bentgrass varieties. The bentgrass plots were mowed at a bench setting of 0.120 inch with a Toro 1000 walk behind greens mower. Also, there were three plots (measuring 4 feet by 6 feet each) for each of the 125 different varieties.

Prior to the application of any product, it was observed that the entire area contained significant amounts of moss colonies ranging in size from small colonies under an inch in diameter to a few larger colonies measuring over 3 inches in diameter. A composition the same as formulation 8 in the previous example was applied to the entire area in two week intervals using a conventional golf course sprayer. After about 6 weeks and 3 applications, it was observed that the moss was well under control with a dramatic reduction in total moss count. Most of the smaller moss colonies had been completely eradicated. There were a few extremely large colonies which measured over 3 inches in diameter which took several more spot treatments to kill. Additionally we did not observe any damage to any of the varieties of grass in the study. We concluded from this study that the present invention is safe and effective when applied to a variety of turfs of the type commonly used on golf course putting greens.

Although the invention has been described in detail in the foregoing embodiments for the purpose of illustration, it is to be understood that such detail is solely for that purpose and that variations can be made therein by those skilled in the art without departing from the spirit and scope of the invention except as it may be limited by the claims.

I claim:

1. A method of controlling moss comprising applying a moss controlling amount of a composition concurrently, comprising:
    (a) a nitrogen containing non foliar fertilizer such as IBDU,
    (b) a non-ionic surfactant or wetting agent,
    (c) a metal containing salt, and
    (d) an acidic pH adjusting agent effective to adjust the pH of the composition to a pH of between 2.5 and 5; wherein said pH adjusting agent comprises a member selected from the group consisting of hydrochloric acid, phosphoric acid, citric acid, acetic acid, and tartaric acid;
    wherein such method substantially completely controls moss in less than about eight weeks and further wherein said metal containing salt is applied in an amount of at least about 30 or more ounces by weight per 1000 square feet of treatment area.

2. The method of claim 1, wherein the metal containing salt is a metal sulfate.

3. The method of claim 2, wherein the metal sulfate is selected from the group consisting of copper sulfate, zinc sulfate, and iron sulfate.

4. The method of claim 1 wherein said applying is by spraying.

* * * * *